US010625006B2

(12) United States Patent
Blümler et al.

(10) Patent No.: US 10,625,006 B2
(45) Date of Patent: Apr. 21, 2020

(54) DEDICATED REMOTE CONTROL OF A PLURALITY OF MEDICAL APPARATUSES

(71) Applicant: Fresenius Medical Care Deutschland GmbH, Bad Homburg (DE)

(72) Inventors: Holger Blümler, Friedrichsdorf (DE); Jürgen Klewinghaus, Oberursel (DE)

(73) Assignee: Fresenus Medical Care Deutschland GMBH, Bad Homburg (DE)

( * ) Notice: Subject to any disclaimer, the term of this patent is extended or adjusted under 35 U.S.C. 154(b) by 0 days.

(21) Appl. No.: 15/592,808

(22) Filed: May 11, 2017

(65) Prior Publication Data
US 2018/0001010 A1 Jan. 4, 2018

(30) Foreign Application Priority Data
Jun. 30, 2016 (DE) .................. 10 2016 111 971

(51) Int. Cl.
G05B 11/01 (2006.01)
A61M 1/16 (2006.01)
(Continued)

(52) U.S. Cl.
CPC ............ A61M 1/1601 (2014.02); A61M 1/14 (2013.01); A61M 1/28 (2013.01); G08C 23/04 (2013.01);
(Continued)

(58) Field of Classification Search
CPC .................. A61M 1/1601; A61M 1/28; A61M 2205/3569; A61M 2205/3592;
(Continued)

(56) References Cited

U.S. PATENT DOCUMENTS 5,987,519 A 11/1999 Peifer et al.
8,667,541 B1 * 3/2014 Zhu .................... H04N 21/4524
455/456.2
(Continued)

FOREIGN PATENT DOCUMENTS

DE 10 2011 107795 A1 1/2013
DE 10 2014 216887 B3 11/2015
(Continued)

OTHER PUBLICATIONS

Hong et al., "Point and Control: The Intuitive Method to Control Multi-device with Single Remote Control," J.A. Jacko (Ed.): *Human-Computer Interaction, Part III*, pp. 416-422, Springer-Verlag Berlin Heidelberg (2009).
(Continued)

*Primary Examiner* — Kerri L McNally
*Assistant Examiner* — Thang D Tran
(74) *Attorney, Agent, or Firm* — Leydig, Voit & Mayer, Ltd.

(57) ABSTRACT

The present invention relates to a method for contactlessly establishing a coupling between a medical apparatus (e.g., a hemodialysis apparatus or a peritoneal dialysis apparatus) and a remote control apparatus. An optical coupling signal is exchanged between the involved communication entities, in order to establish bijective, data-processing coupling between the remote control apparatus and the medical apparatus. Only after successful coupling is a remote control procedure initiated for remote control of the medical apparatus.

25 Claims, 4 Drawing Sheets

(51) Int. Cl.
*A61M 1/14* (2006.01)
*H04W 12/00* (2009.01)
*G16H 40/67* (2018.01)
*A61M 1/28* (2006.01)
*G08C 23/04* (2006.01)
*H04L 29/06* (2006.01)
*G16H 20/40* (2018.01)

(52) U.S. Cl.
CPC ............. *G16H 40/67* (2018.01); *H04L 63/08* (2013.01); *H04L 63/105* (2013.01); *H04W 12/0052* (2019.01); *A61M 2205/3569* (2013.01); *A61M 2205/3592* (2013.01); *A61M 2205/50* (2013.01); *A61M 2205/502* (2013.01); *A61M 2205/6063* (2013.01); *G08C 2201/20* (2013.01); *G08C 2201/30* (2013.01); *G08C 2201/50* (2013.01); *G08C 2201/71* (2013.01); *G08C 2201/92* (2013.01); *G08C 2201/93* (2013.01); *G16H 20/40* (2018.01)

(58) Field of Classification Search
CPC ........ A61M 2205/50; A61M 2205/502; A61M 2205/6063; A61M 1/14; G08C 23/04; G08C 2201/20; G08C 2201/30; G08C 2201/50; G08C 2201/71; G08C 2201/92; G08C 2201/93; H04L 63/08; H04L 63/105; G16H 40/67; G16H 20/40; H04W 12/0052
USPC ...................................................... 340/12.52
See application file for complete search history.

(56) References Cited

U.S. PATENT DOCUMENTS

| | | | |
|---|---|---|---|
| 8,905,959 | B2 | 12/2014 | Basaglia |
| 9,189,597 | B2 | 11/2015 | Bluemler et al. |
| 9,549,324 | B2 | 1/2017 | Birtwhistle et al. |
| 9,635,111 | B2 | 4/2017 | Wang et al. |
| 9,800,663 | B2* | 10/2017 | Arrizza ............... A61M 1/1603 |
| 9,974,622 | B2* | 5/2018 | Franjic .................. A61B 42/10 |
| 10,173,008 | B2 | 1/2019 | Simpson et al. |
| 2005/0080403 | A1* | 4/2005 | Takahashi ............. A61B 17/00 606/1 |
| 2005/0182366 | A1* | 8/2005 | Vogt ..................... A61M 5/142 604/131 |
| 2005/0283203 | A1* | 12/2005 | Flaherty ............ A61B 5/04001 607/48 |
| 2006/0056855 | A1* | 3/2006 | Nakagawa ................ G09F 9/33 398/183 |
| 2007/0185545 | A1 | 8/2007 | Duke |
| 2009/0060515 | A1* | 3/2009 | Tsurumoto ............ G08C 17/02 398/106 |
| 2009/0076461 | A1* | 3/2009 | Susi .................. A61M 5/14228 604/246 |
| 2009/0085765 | A1* | 4/2009 | Bruhn .................... G08C 23/04 340/12.22 |
| 2009/0099864 | A1* | 4/2009 | Cronrath ................... G06F 8/60 705/2 |
| 2009/0221914 | A1* | 9/2009 | Barrett .................. A61M 5/007 600/431 |
| 2009/0306573 | A1 | 12/2009 | Gagner et al. |
| 2010/0022937 | A1* | 1/2010 | Bedingfield ............ A61M 1/16 604/6.09 |
| 2010/0268383 | A1* | 10/2010 | Wang ........................ B25J 5/00 700/248 |
| 2011/0006876 | A1* | 1/2011 | Moberg .............. G06F 19/3406 340/3.2 |
| 2012/0118718 | A1* | 5/2012 | Geiger ................. H01H 36/004 200/5 A |
| 2012/0278759 | A1* | 11/2012 | Curl ...................... G06F 19/327 715/804 |
| 2012/0323212 | A1* | 12/2012 | Murphy .................. A61M 5/00 604/500 |
| 2013/0018355 | A1* | 1/2013 | Brand .................... G16H 40/67 604/500 |
| 2013/0244580 | A1* | 9/2013 | Yanagidate ........ A61B 1/00016 455/41.3 |
| 2013/0251373 | A1 | 9/2013 | Yano et al. |
| 2013/0317753 | A1* | 11/2013 | Kamen ................. G06F 3/0481 702/19 |
| 2013/0331778 | A1* | 12/2013 | Kruse .................. A61M 5/1413 604/66 |
| 2014/0266983 | A1* | 9/2014 | Christensen ........ A61M 1/3609 345/8 |
| 2014/0267003 | A1* | 9/2014 | Wang ...................... G06F 3/017 345/156 |
| 2014/0276375 | A1* | 9/2014 | Minkus ............... A61M 1/1682 604/28 |
| 2014/0288947 | A1* | 9/2014 | Simpson ............. G06F 19/3418 705/2 |
| 2015/0002606 | A1* | 1/2015 | Hyde .................. G06F 19/3418 348/14.02 |
| 2015/0112264 | A1* | 4/2015 | Kamen .................. G16H 20/17 604/151 |
| 2015/0180880 | A1* | 6/2015 | Nakano .................. G08C 17/02 726/4 |
| 2015/0199485 | A1* | 7/2015 | Borges .................. G16H 40/63 600/323 |
| 2015/0304478 | A1* | 10/2015 | Kim ........................ H04W 4/80 455/414.3 |
| 2016/0038675 | A1* | 2/2016 | Estes .................... A61M 5/1413 604/506 |
| 2016/0066893 | A1* | 3/2016 | Cho ........................ A61B 8/54 600/459 |
| 2016/0206800 | A1* | 7/2016 | Tanenbaum ........ A61M 1/1601 |
| 2016/0246943 | A1* | 8/2016 | Lake ................... G06F 19/3418 |
| 2016/0261974 | A1* | 9/2016 | Arrizza .................. H04W 4/008 |
| 2016/0328958 | A1* | 11/2016 | Ruch ...................... G08C 17/02 |
| 2016/0350503 | A1* | 12/2016 | Jun ...................... G06F 3/04883 |
| 2017/0120002 | A1* | 5/2017 | Barak .................... A61M 25/00 |
| 2017/0290980 | A1* | 10/2017 | Friedli ................. A61M 5/1723 |
| 2018/0015218 | A1* | 1/2018 | Welsch ................. A61M 5/172 |

FOREIGN PATENT DOCUMENTS

EP          1 312 332 A1    5/2003
WO    WO 2014/195126 A1   12/2014

OTHER PUBLICATIONS

International Patent Application No. PCT/EP2017/065692, Search Report (dated Aug. 17, 2017).
German Patent Application No. 102016111971.7, Examination Report (dated Sep. 18, 2018).

* cited by examiner

DEDICATED REMOTE CONTROL OF A PLURALITY OF MEDICAL APPARATUSES

CROSS-REFERENCE TO RELATED APPLICATIONS

Priority is claimed to German Patent Application No. DE 102016111971.7, filed on Jun. 30, 2016, the entire disclosure of which is hereby incorporated by reference herein.

FIELD

The present invention is directed to the field of medical technology and relates in particular to medical apparatuses and the electronic control thereof. The invention relates in particular to a method for producing a contactless coupling between a mobile remote control apparatus and at least one medical apparatus, and to a remote control apparatus designed for the remote control of the medical apparatus, a medical apparatus and a remote control system.

BACKGROUND

In medical technology, it is known to operate medical apparatuses, such as dialysis apparatuses, via remote control. It has hitherto proven to be disadvantageous that in each case a specific remote control apparatus was required for a specific dialysis apparatus. This is due primarily to safety aspects and to ensure that, on the one hand, no germs are transmitted and that, on the other hand, no unauthorized access to the dialysis apparatus takes place. Since life-sustaining measures for the patient are occasionally performed on the dialysis apparatus or on other medical apparatuses, it should be ensured that no unauthorized access can be gained to the dialysis apparatus via the remote control apparatus. Basically, different functions on the dialysis apparatus can be remote controlled, such as controlling entertainment functions for the patient during a dialysis treatment, processing alarm indications and basically all functions which can be controlled by a user via the user interface of the medical apparatus.

In practice, a plurality of dialysis apparatuses are typically used in parallel in one room—a so-called dialysis station. If a separate remote control then has to be used for each one of the dialysis apparatuses, this proves to be very cumbersome in practice because the different remote control apparatuses can become mixed up or be mislaid, thus making remote control no longer possible. Therefore, from the point of view of the user, a universal remote control for a group of medical apparatuses is expedient.

In order to avoid this problem, it is known in the prior art to provide a remote control which is coupled to the apparatus, which is to be remote controlled in each case, in a preparatory phase. The coupling process or pairing process serves to establish bijective coupling between the medical apparatus to be remote controlled and the remote control apparatus. If a universal remote control is to be used for a group of different medical apparatuses, then prior to using the remote control apparatus a specific pairing code is input into the remote control apparatus in order to be able to establish a specific coupling between the remote control apparatus and the medical apparatus to be remote controlled. However, this previous approach proves to be impractical because it is not possible to react rapidly using the remote control because initially the pairing code must be input prior to each remote control operation.

In the field of entertainment electronics, it is known in particular to provide universal operation for different electronic apparatuses. For instance, it is known in particular from the publication "*Point and Control: The Intuitive Method to Control Multi-device with Single Remote Control*" Sung Soo Hong, Ju Il Eom, User Interface Lab, Digital Media and Communication R&D Center, Digital Media and Communication Business, Samsung Electronics Co. Limited, 416, Maetan-3 Dong, Suwon-City, to provide universal remote control in the form of a key-controlled small unit, in order to remote control different electronic apparatuses (televisions, video recorders etc.). As already mentioned above, a pairing process is provided in order then to be able to adjust the universal remote control specifically to the remote control of the electronic apparatus to be remote controlled in each case. The Samsung document defined above describes a Point and Control controller (PAC controller) which requires the remote controller to be directed initially to the electronic apparatus to be remote controlled, in order to exchange coupling information. This can be accomplished by the transmission of an optical key or key code; in this case this is done through the exchange of infrared light-emitting diode (LED) signals. After completion of the pairing process, remote control of the electronic apparatus can be effected. As is generally known and also illustrated in FIG. 5 of the Samsung document, the remote control apparatus is equipped for this purpose with operating elements (sliding controller, buttons and the like), in order to remote control the electronic apparatus 210, 220, 230 (see FIG. 5 of the Samsung document).

However, such a method which is expedient for general electronic apparatuses cannot be used in medical technology for safety reasons due to safety criteria for the medical field. On the one hand, it should be ensured that only authorized accesses to a specific medical apparatus can be acquired by authorized users via the respective remote control apparatus. It should also be ensured that the respective remote control apparatus also controls the intended dialysis apparatus and no other apparatus which is possibly located in the same room and likewise can be coupled to the remote control apparatus. In so doing, it should be ensured that the operation of the medical apparatus—either directly or indirectly via the remote control apparatus—does not transmit any pathogenic organisms and cross-contamination does not occur.

Previously, the medical apparatus had to be operated directly by contact with an operating element on the apparatus itself. This requires contact with the apparatus which, in principle, carries the risk of transmission of germs, in that, for example, a user of a first medical apparatus operates a further medical apparatus without disinfecting beforehand and therefore can transmit, for example, pathogenic germs or microorganisms to the second apparatus which could then ultimately be transmitted to the patient. Against this background, it is important to permit contactless apparatus coupling for remote operation and remote control of the medical apparatus, in order to avoid cross-contamination by a number of users of a common operating interface (for different medical apparatuses and patients).

A further aspect which does not allow known solutions form other fields of technology (such as general entertainment electronics) to be applied to the field of medical technology can be seen in the fact that dialysis apparatuses or other medical apparatuses are frequently used to perform life-sustaining measures. A secure and bijective control function or remote control is thus utilized. Typically, the medical apparatus is operated via a graphical user interface which allows the user to be able to effect his inputs on a display screen. Therefore, it is desirable that the remote control apparatus likewise has an approximately similar user interface which is adapted to the interface of the respective medical apparatus.

SUMMARY

In an exemplary embodiment, the invention provides a method for contactlessly establishing a coupling between a mobile remote control apparatus and a medical apparatus from a group of medical apparatuses for dedicated remote control of the medical apparatus on the remote control apparatus. The method includes: exchanging a directed optical coupling signal between the remote control apparatus and the medical apparatus, in order to initiate a bijective coupling between the remote control apparatus and the medical apparatus; and establishing the bijective coupling between the remote control apparatus and the medical apparatus.

In another exemplary embodiment, the invention provides a remote control apparatus for remote control of a medical apparatus of a multiplicity of medical apparatuses. The remote control apparatus includes: an interface, configured to exchange a directed optical coupling signal with the medical apparatus in order to establish a bijective coupling between the remote control apparatus and the medical apparatus; and a processor, configured to initiate a remote control procedure after the bijective coupling between the remote control apparatus and the medical apparatus has been established.

In yet another exemplary embodiment, the invention provides a medical apparatus. The medical apparatus includes: a signal exchanger, configured to facilitate establishment of a bijective coupling between a remote control apparatus and the medical apparatus via a directed optical coupling signal; and a processor, configured to establish the bijective coupling between the remote control apparatus and the medical apparatus.

In yet another exemplary embodiment, the invention provides a remote control system for medical apparatuses. The remote control system includes: a group of medical apparatuses, wherein all or selected ones of the medical apparatuses comprise a signal exchanger and a processor; and at least one remote control apparatus, configured for remote control of at least one of the medical apparatuses, wherein the at least one remote control apparatus comprises an interface and a processor.

BRIEF DESCRIPTION OF THE FIGURES

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
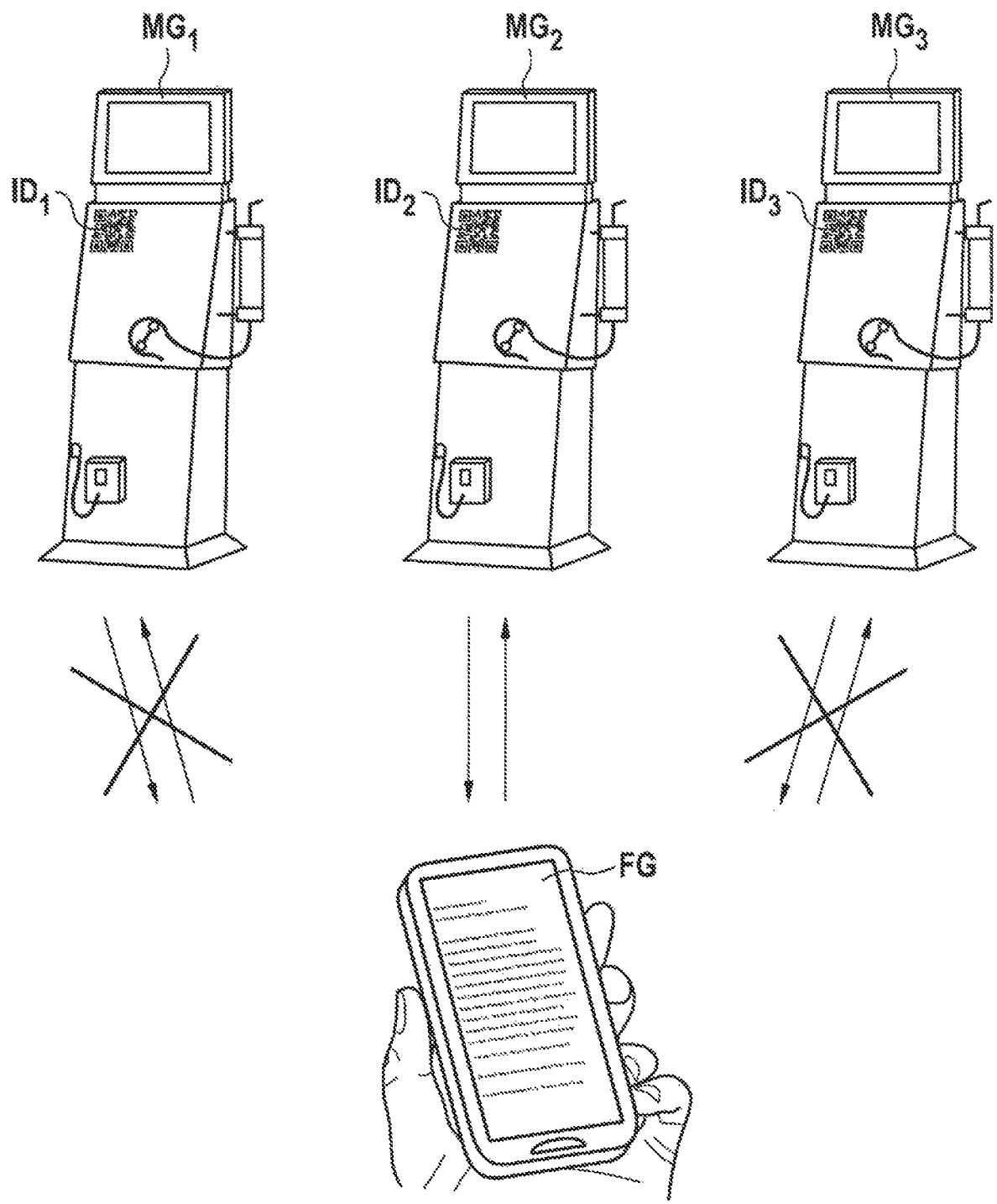
FIG. 1 shows an overview of a remote control system of a plurality of medical apparatuses with one remote control apparatus.

Exemplary embodiments of the present invention provide a remote control option for medical apparatuses which satisfies the safety criteria for medical apparatuses and which is also practical and efficient to use. In particular, exemplary embodiment of the present invention provide for remote control of a plurality of medical apparatuses in a specific and contactless manner using one remote control apparatus, in order to be able to reliably avoid cross-contamination.

In an exemplary embodiment, the present invention provides a method of contactlessly establishing a coupling between a mobile remote control apparatus and at least one medical apparatus from a group of medical apparatuses for dedicated remote control of the respective medical apparatus. Other exemplary embodiments include a remote control apparatus, a medical apparatus and a remote control system.

It will be appreciated that features of an exemplary embodiment of the present invention described with respect to a method may also apply to exemplary embodiments of the invention corresponding to the remote control apparatus, the medical apparatus, and the remote control system. For example, respective apparatus modules or electronic hardware modules, such as microprocessor apparatuses and the like, which are implemented in the apparatus or in the system, may be configured to perform the described steps of the method.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein performed by computing devices and components thereof may be carried out according to stored instructions and/or installed applications.

Exemplary embodiments of the present invention provide a contactless coupling process between a universal remote control apparatus and a specific medical apparatus, preferably a dialysis apparatus. For this purpose, the medical apparatus and the remote control apparatus are equipped with optical components which recognize when the remote control apparatus is being directed to the medical apparatus to be remote controlled in each case, in order thereupon to initiate a coupling process in a dedicated manner, in order then to remote control the medical apparatus in a control phase via the remote control apparatus.

In a first exemplary embodiment, the invention provides a method of contactlessly establishing a coupling between a mobile remote control apparatus and a specific medical apparatus, in particular a dialysis apparatus, from a group of medical apparatuses for dedicated remote control of the (specific) medical apparatus on the remote control apparatus. The method includes:

exchanging a directed optical coupling signal between the remote control apparatus and the respective medical apparatus, in order to establish a bijective data-processing coupling between the remote control apparatus and the medical apparatus;

establishing the coupling between the remote control apparatus and the medical apparatus.

Exemplary embodiments of the invention avoid cross-contamination. Since the remote control apparatus is a universal remote control apparatus which, in principle, can also be used for different dialysis apparatuses or other medical apparatuses, there is basically the risk of germs and pathogenic organisms being exchanged. Therefore, the coupling process and the remote control process should avoid requiring operating contacts (by different users). Therefore, the coupling is established in a contactless manner between the remote control apparatus and the medical apparatus. This means that the user does not have to effect any inputs on a (graphical) user interface. In one exemplary embodiment, the remote control apparatus is directed to the medical apparatus to be remote controlled in each case, so that optical signals or other radio signals can be exchanged between the two apparatuses, in order to perform the coupling process in a bijective manner. In this case, the term "bijective" denotes a reversible uniqueness, so that in mathematical terms precisely one medical apparatus is allocated to precisely one coupled remote control apparatus.

In a preferred embodiment, the medical apparatus relates to a dialysis apparatus. This can relate to different types of dialysis apparatus, such as a hemodialysis apparatus or a peritoneal dialysis apparatus. However, exemplary embodiments of the invention are also applicable to other medical, computer-controlled apparatuses, such as fluid management machines, blood treatment apparatuses or other medical machines. Preferably, the medical apparatuses have a (graphical) user interface which can be formed as a touch-screen. For operating purposes, in particular a capacitive touch-screen comprising multi-sensor functionality is provided, in which even simultaneous touches on the touch-sensitive interface can be detected. An example of such a touch-screen is described in more detail in U.S. Pat. No. 9,189,597, which is incorporated by reference herein in its entirety. Provided on the display are interaction surfaces, switching elements, control fields and further input and output fields which are used for controlling the medical apparatus. The touch-screen thus serves both to input user commands and signals and also to output messages of the medical apparatus to the user. The messages can be, for example, alarm indications, messages to be acknowledged or other status messages. The medical apparatus can also be used in different types. For instance, a hemodialysis apparatus type 5008 from Fresenius Medical Care, a further hemodialysis apparatus from the same or other manufacturer and possibly of a different type can be used, for example, in one dialysis station. All apparatuses can have a slightly different user interaction, operating control and/or user interface for controlling the apparatus.

In an exemplary embodiment, the remote control apparatus is designed as a mobile apparatus. The remote control apparatus is an electronic unit which has a plurality of interfaces, in particular wireless interfaces (e.g. via radio links, wireless local area network (WLAN), optical connections, etc.). In particular, it can be a smartphone, a tablet, a personal digital assistant (PDA), or other electronic apparatuses. The electronic remote control apparatuses preferably have a user interface, in particular a graphical user interface. Furthermore, in a preferred embodiment the remote control apparatuses are formed having an optical sensor, in order to be able to receive and process optical signals from the medical device. In particular, this can be a camera.

The coupling between the remote control apparatus and a specific medical apparatus is bijective in mathematical terms. This means that a specific medical device from a group of medical devices (e.g. in a dialysis room) is allocated to a specific remote control apparatus (a plurality of remote control apparatuses can also be provided). This constitutes a data-processing coupling between the remote control apparatus and the medical device. In accordance with one embodiment of the invention, only one medical apparatus can ever be coupled to a remote control apparatus, in order to reliably avoid unauthorized accesses. In accordance with another embodiment of the invention, it is also possible to be able to provide a so-called multiple remote control functionality, so that a plurality of remote control apparatuses can also remote control one and the medical apparatus (e.g. for training purposes). The coupling or the coupling process defines in data-processing terms the two communication partners—i.e. the respective medical apparatus and the remote control apparatus. After successful coupling, the remote control apparatus thus "knows" with which medical apparatus it is communicating, and vice versa. In more complex embodiments, further apparatus parameters can also be exchanged in this case between the remote control apparatus and the medical apparatus. In particular, the medical apparatus can transmit medical apparatus-related parameters to the remote control apparatus and the remote control apparatus can transmit remote control apparatus-related parameters to the medical apparatus, in order, for example, to request specific apparatus settings which can then be taken into consideration in the remote control operation.

As a result, the coupling process leads to the establishment of a coupling between the remote control apparatus and the respective medical apparatus. Only after the coupling has been successfully established can the medical apparatus be remote controlled via the remote control apparatus. For this purpose, a control channel for exchanging control signals for the dedicated remote control of the medical device is established by the remote control apparatus. The control channel is used in particular for the bidirectional exchange of control signals. However, in simple embodiments provision can also be made that either "only" the medical apparatus transmits messages (to be acknowledged on the remote control apparatus) to the remote control apparatus or that "only" the remote control apparatus transmits control signals to the medical apparatus.

In a preferred embodiment of the present application, the coupling signal is a bundled or collimated beam of light. It may be generated by a light source having a component for light bundling or light collimation in order to focus and concentrate the light—for example, optical lenses, collimators, etc. With a collimated coupling signal it is possible to specifically address one particular medical device of the devices and thereby ensure that the user is in visual contact with the respective receiving device of the coupling signal. Relating thereto as an advantage, safety of the remote control process may be increased.

The remote control of the medical apparatus can be subdivided into two time phases:
1. a coupling phase which serves to exchange confirmation signals, acknowledgement signals, identification codes and prompt signals and request signals and further characteristics of the communication apparatuses involved. Only after the successful completion of the coupling phase can the following second phase be initiated, namely the:
2. control phase in which the medical device is actually remote controlled using the remote control apparatus. For this purpose, a control channel is established, via which control signals can be exchanged between the communication apparatuses involved. In a preferred embodiment, the control channel is based on a different transmission technology than the transmission channel for performing the coupling process. In particular, the transmission channel for performing the coupling process is an optical channel.

This has the substantial advantage that the coupling process can be performed very efficiently and above all in a contactless manner, whereas the actual remote control can likewise be performed efficiently and reliably and can be operated via radio technology, for example, WLAN.

In order to signify a successful coupling process, provision is made in a preferred embodiment of the invention to detect and output a coupling state. Depending upon the embodiment, different aspects in the coupling state can be represented. On the one hand, it is possible to represent that successful coupling has taken place between the medical apparatus and the remote control apparatus and therefore remote control of the medical apparatus is activated and possible. In other embodiments, it is possible to signify that a coupling process is just being performed. In another embodiment, it is possible to signify that at the moment remote control of the medical apparatus is just being performed by a remote control apparatus. It is also possible to combine the aforementioned embodiments in one common embodiment, so that the coupling state represents that successful coupling has taken place, that at the moment coupling is just being initiated and performed and/or that at the moment remote control is just being performed.

In order to ensure safe operation by only authorized persons, provision is made in the preferred embodiment that only one coupling is possible in one time phase. This means that no further remote control apparatus can be coupled to the medical apparatus, if a coupling is established between the respective medical apparatus and a first remote control apparatus. Basically, not only can the remote control apparatus be designed for one medical apparatus, it can also be used for remote control of other medical apparatuses. Therefore, in accordance with a preferred embodiment of the invention provision is made that the remote control apparatus can be coupled only to one medical apparatus during a specific time phase. In particular—if a user inputs control commands for a specific medical apparatus on a remote control apparatus—it should not be possible for other medical apparatuses to also be controlled thereby in an unintended manner at the same time.

However, there are certainly situations of usage in which multiple remote control is desired. This is the case, for example, if trainee users (e.g. nurses) are to receive training, in that their remote control inputs are to be monitored by a monitoring person. The monitoring person can be using a different remote control apparatus. In this case, provision is made that the same medical apparatus is controlled by a plurality of remote control apparatuses. Since multiple remote control is a very sensitive procedure, provision is made in a preferred embodiment that this multiple remote control is represented by a corresponding multiple remote control signal. The multiple remote control signal can likewise also be incorporated into the coupling state and be taken into consideration therein. In particular, provision is made that a corresponding multiple remote control signal is output if more than two remote control apparatuses remote control the same medical apparatus. The coupling state can be output only on the respective medical apparatus, only on the remote control apparatus or on both apparatuses. This increases system security because it is directly and immediately apparent on the devices involved if remote control is intended. The coupling state can be output via different output media, for example, as an optical signal (LED), acoustic signal or in combined form or on other output mechanisms.

Since—as already mentioned above—it is a special application if multiple remote control is desired, provision is made in a preferred embodiment of the invention that a presetting is implemented which offers the option of multiple remote control functionality only as a specifically selectable function. It is preset for multiple remote control to be precluded. In other words, in this embodiment it is precluded during an existing coupling for one or further remote control apparatus(es) to be able to connect to the respectively coupled medical apparatus for remote control purposes.

In accordance with one advantageous embodiment of the invention, the exchange of the directed coupling signal is based on a transmission of a directed, optical prompt signal which is transmitted by the remote control apparatus to the medical apparatus. In this embodiment, the coupling is thus initiated by the remote control apparatus, in that a corresponding prompt command is transmitted by the remote control apparatus.

In accordance with an alternative embodiment of the invention, the directed coupling signal is exchanged by reception of an identification code on the remote control apparatus which unequivocally identifies the respective medical apparatus. In this embodiment, the medical apparatus is designed having an identification code which can be provided, for example, as an optical code (in graphical form, for example, as a QR code or bar code). This identification code is then detected by an optical sensor (e.g. a camera) on the remote control apparatus. In this embodiment, the coupling process can also be triggered by the remote control apparatus, in that the remote control apparatus initiates the coupling procedure via an activation signal. The activation signal can be, for example, a user-operable switch, via which the user can trigger the coupling procedure. If this switch is switched to "ON", the camera is activated and serves to detect the identification code of the respective medical apparatus. If no such activation signal is present (because, for example, the switch is in the "OFF" position), provision can be made that the camera is deactivated in order to be able to avoid unnecessary data captures. When activated, the camera of the medical apparatus serves to detect the identification code which denotes and characterizes the respective medical apparatus in a bijective manner. Therefore, the remote control apparatus "knows" with which medical apparatus it is to communicate and control.

The coupling signal is, for example, preferably an optical signal (e.g. as an infrared signal). Alternatively, it can be a different type of signal, for example, an acoustic signal at a specific frequency or a digital code.

Furthermore, the remote control apparatus is configured to decode the—preferably graphical—identification character or the identification code of the medical apparatus, in order to be able to identify the respective medical apparatus unequivocally in order then to be able to initiate the coupling process specifically and in a dedicated manner with regard to the respective medical apparatus. The coupling procedure is this preferably always configured to be dedicated to a specific medical apparatus. This can be effected, for example, by exchanging WLAN keys, wherein in each case a WLAN key is unequivocally allocated to the identified medical apparatus, or by exchanging other identifiers and/or keys in corresponding connection protocols.

The identification code provided on the medical apparatus characterizes and identifies the respective medical apparatus in an unequivocal manner. In order to detect the identification code on the remote control apparatus, the remote control apparatus has a corresponding sensor formed thereon which serves to read-in the identification code. If the identification code is a QR code, an optical sensor can be formed; otherwise, if the identification code is a bar code, a corresponding sensor, a bar code scanner, is formed on the medical apparatus.

In a further exemplary embodiment, the medical apparatus transmits a confirmation signal to the remote control apparatus after exchanging the—preferably optical—coupling signal. However, the remote control apparatus is designed to receive the confirmation signal. The reception of the confirmation signal can also be incorporated in the coupling state and can also be output as a signal. In a further embodiment, provision can be made that an acknowledgement signal is output after reception of the confirmation signal. The acknowledgement signal can be output either directly on the remote control apparatus (e.g. as an optical signal) or can be transmitted to the medical apparatus. A setting can be effected to allow the further coupling procedure and in particular the establishment of the control channel to be established only after reception of the confirmation signal and/or only after reception of the acknowledgement signal. In this way, a higher level of security of the coupling procedure can be achieved. In particular, it is possible for a user to have the option to intervene manually if he notices from the output of the coupling state that incorrect coupling is about to be performed. Then, the coupling procedure can be interrupted, so that the control channel cannot be established. The confirmation signal and/or the acknowledgement signal can be optical signals or acoustic signals. In order not to disrupt the dialysis sequence, which where possible is not disrupted, by remote control coupling processes to be performed, preferably optical signals are used as the confirmation signal and acknowledgement signal.

As already explained above, it is basically possible for the remote control to be universal, so that it can be used for remote controlling different medical apparatuses. To this end, provision can be made that characteristic command sets for controlling the different medical apparatuses are stored. Depending on which medical apparatus is to be controlled, the respectively allocated command set is then selected. However, it is also possible for the identification code to contain an addition which signifies which command set may be used for remote control purposes. Therefore, specific command sets (which include, for example, an excessively large remote control scope) can be precluded. Alternatively, it is also possible for this information to be coded for using the remote control command set in the confirmation signal. The different command sets can be stored either immediately and directly in a memory of the remote control apparatus. Alternatively, the different command sets can be stored on a server, with which the remote control apparatus exchanges data. This has the advantage that the command sets can be changed without a change measure having to be performed on the remote control apparatus. Furthermore, the command sets can be centrally managed. In this embodiment, the command sets can be provisioned, for example, in a central database.

The control channel is thus created and established in response to and in dependence upon the characteristics of the medical apparatus to be remote controlled in each case. Depending upon which parameters and signals have been transmitted in the identification code, for example, a specific command set for remote control purposes can be selected and brought into use. Furthermore, the identification code can define that only specific remote control commands can be used. For example, for medical crisis situations it can be preset that remote control can be performed only for non-critical commands.

By specifically coupling the medical apparatus to the remote control apparatus, it is possible to apply the remote control procedure in a dedicated manner to the medical apparatus to be remote controlled in each case. To this end, provision can be made in an exemplary embodiment that the optical prompt signal includes a request signal (or that a request command can be generated from the prompt signal). The request command serves to request parameters of the medical apparatus and to provide them on the remote control apparatus, said parameters representing specific technical characteristics of the medical apparatus and/or its user and/or the situation of use. The characteristics can be, for example, the occurrence of a medical crisis intervention or an authorization level of the user or technical parameters of the medical apparatus. The control channel can then be specifically established in dependence upon the respectively detected parameters. This can preclude unauthorized control actions from being performed via the remote control apparatus.

Remote control is generally performed via a sequence of individual remote control actions. The individual remote control actions can relate, for example, to specific commands for the medical apparatus (such as "operate control element", "acknowledge message", "activate infusion pump", "initiate, interrupt, terminate dialysis procedure", etc.). Basically, remote control of the medical apparatus takes place within the scope of use of the medical apparatus—i.e. during dialysis or preparation for dialysis. Therefore, specific operating actions of the medical apparatus can be performed directly on the medical apparatus or even by remote control on the remote control apparatus. In order to increase the security of the entire system, in an exemplary embodiment, the method includes an option in which all operating or control actions performed are retained in a log file. In a further advantageous embodiment of the invention, provision can be made that the information relating to which control action has been initiated by which apparatus is additionally stored. Therefore, it is possible to understand which commands have been executed as remote control commands and which commands have been used directly on the medical apparatus. This has the advantage that incorrect operations can also be possibly more easily understood in hindsight, thus also making an allocation to the respective user possible.

In an advantageous manner, within the scope of the remote control each performed command is allocated a characteristic action code and is stored in a memory. This facilitates the logging of control commands and the allocation of control commands to an apparatus (e.g. remote control apparatus).

In a further advantageous embodiment of the invention, the remote control should be adapted as extensively as possible to the direct control of the medical apparatus. To this end, preferably the (graphical) user interface of the medical apparatus is transferred to the remote control apparatus. Therefore, the user can input the same commands on the remote control apparatus as he can on the medical apparatus. Therefore, he does not have to readjust to a different user interface but instead can use his "usual" user interface. However, it is also possible that the user interface of the medical apparatus is not transferred completely to the remote control apparatus, because unnecessary and irrelevant data are possibly also transmitted therewith, but instead that only a section or a part of the user interface of the medical apparatus is transmitted. Preferably, only a relevant section of the user interface is transmitted to the remote control apparatus. For instance, provision can be made that only those sections are transmitted which are to be specifically operated in a specific time phase. The other sections of the user interface are then displayed on the remote control apparatus. The transmission capacity between the medical apparatus and the remote control apparatus can thus be reduced.

In a further advantageous embodiment of the invention, the scope of the remote control can be limited or extended. The limitation or extension can be dependent on the authorization level the user of the remote control apparatus has. To this end, the authorization level is detected by an authorization signal. This can be effected automatically, in that the dial-in data of the respective user are detected on the remote control apparatus and an authorization signal is derived therefrom—possibly by access to a central database. In a preferred embodiment of the invention, an authorization level determining unit, which may be referred to as "an authorization level meter," is integrated into the remote control apparatus. The authorization level meter serves to automatically ascertain the authorization level, in order to determine the functionality of the remote control in dependence upon the ascertained authorization level. The authorization level meter can comprise an identifier. The identifier serves initially to establish the identity of the operator. Using this identity information, the authorization level meter can then ascertain the respectively allocated authorization level—typically by access to a memory or a database. The identifier can be formed, for example, as a fingerprint scanner which is arranged on the remote control apparatus or exchanges data therewith. Alternatively, the operator can carry a pager or an radiofrequency identification (RFID) tag which identifies him and relays these identification signals to the authorization level meter for processing purposes. Alternatively, the identification of the operator can be configured via the identifier by processing biometric data or by a personal identification number (PIN) or transaction authentication number (TAN) code or by a different identification signal.

The authorization signal denotes which commands the user can perform. For example, the situation can arise that a nurse is authorized only for specific instructions, whereas a senior doctor can perform a broader spectrum of commands. However, the limitation or extension of the remote control functionality not only can be made dependent upon the detected authorization signal, but can also be effected in response to the detected confirmation signal or the detected identification code of the medical apparatus. For example, it is possible that a flag is placed or not placed in the confirmation signal and/or in the identification code, said flag signifying whether a specific command set is to be used or not. Basically, different command sets for performing the remote control of the medical apparatus can be stored. As already explained above, these command sets can be stored directly in the remote control apparatus or in a central database which can be accessed via an interface (e.g. a web interface). The command set can thus be determined in dependence upon the detected authorization level of the user.

For instance, it is possible that an input command of a command set for remote control of the medical apparatus by a first user can be overwritten by a second user in response to a detected correction command of the second user, if the authorization level of the second user is higher than the authorization level of the first user. This embodiment is geared to ensure that the authorization of the respective remote control apparatus user is taken into account when performing the remote control. For example, a regime can be defined which allows a more highly qualified user (e.g. a senior doctor) to restrict the remote control by remote control actions of users of a lower qualification. Likewise, parallel remote control by two different remote control apparatuses can be permitted (multiple remote control functionality). In this case, it is likewise possible to configure which commands have a higher priority and are performed in a preferred manner. It is also possible for collisions between the different commands of the different remote control apparatuses to be resolved, in that the user having the higher authorization level preferably performs the action. In this embodiment, it is possible to provide training to a user having a lower qualification, in that, for example, correction commands of a second user can be input on a second remote control apparatus, said correction commands then preferably being taken into account because the second user has a higher qualification than the first user. For training purposes, provision can be made that in addition a correction signal is provided if a correction command has been performed by a different remote control apparatus. The correction signal is then output on the remote control apparatus, of which the command has been corrected or overwritten so to speak. This renders it possible to inform the first user about the correction of his command.

If the multiple remote control functionality is activated, it is basically possible that the same medical apparatus is controlled by a plurality of remote control apparatuses. Provision can be made that a first remote control apparatus controls a first medical apparatus and subsequently a second remote control apparatus controls the first medical apparatus. However, it is also possible that a remote control apparatus controls a first medical apparatus and at a later stage and subsequently controls a further, second medical apparatus. It is also possible that a remote control apparatus controls a plurality of medical apparatuses in parallel. This proves to be helpful particularly if additional functions are to be performed consistently on all dialysis apparatuses in the dialysis station, such as the activation or deactivation of musical accompaniment or the like. Since the multiple remote control functionality is associated with a high safety risk, provision can be made that the multiple remote control functionality is fundamentally (preset) blocked and can be activated only in response to a specific user input. The user input can require a specific authorization level. It is also possible that the multiple remote control functionality is then deactivated. Basically, the multiple remote control functionality is always represented by the multiple remote control signal, so that it is transparent whether a plurality of remote control apparatuses can remote control the same medical apparatus at the same time.

In accordance with a further advantageous embodiment, during an established coupling between the medical apparatus and a first remote control apparatus, further coupling to a second remote control apparatus can be effected only after a multiple remote control criterion has been successfully verified. Therefore, the safety of the system can be increased, in that unintended multiple remote control actions and inconsistent command inputs are avoided. Thus, exemplary embodiments are able to comply with the increased safety criteria in the field of medicine by restricting or extending the remote control functionality in dependence upon the detected authorization signal.

In an exemplary embodiment, the method includes method steps which are performed on the remote control apparatus and method steps which are performed on the medical apparatus. In particular, the prompt signal which is preferably optical in nature is transmitted by the remote control apparatus to the medical apparatus and received therein. The identification code is transmitted by the medical apparatus to the remote control apparatus and is received and processed on the remote control apparatus. The coupling to the medical apparatus is established in a processing unit of the remote control apparatus in dependence upon the identification code. Subsequently, the control channel can be established between the remote control apparatus and the respectively dedicated medical apparatus. Alternatively, a confirmation signal can be additionally transmitted by the medical apparatus to the remote control apparatus. Furthermore, upon reception of the confirmation signal the remote control apparatus can output an acknowledgement signal or can transmit the acknowledgement signal to the medical apparatus.

In a further aspect, the invention relates to a remote control apparatus for remote control of one medical apparatus of a multiplicity of medical apparatuses. The remote control apparatus comprises:

a coupling unit (e.g., an interface such as a detector or a transmitter) which is configured to exchange a directed coupling signal between the remote control apparatus and the medical apparatus, in order to establish bijective coupling between the remote control apparatus and the medical apparatus; and a processing unit which exchanges data with the coupling unit and is configured to initiate a remote control procedure after coupling between the remote control apparatus and the medical apparatus has been established.

In one advantageous variation, the remote control apparatus comprises a (preferably graphical) user interface which is configured to remote control the medical apparatus. As already mentioned above with reference to the method, the user interface of the medical apparatus can be completely or partially "mapped" or transmitted to the user interface of the remote control apparatus, so that the user does not have to readjust to a different user interface.

In one advantageous embodiment of the invention, the remote control apparatus can comprise an authorization level meter and/or an identifier. The identifier serves to automatically determine the identity of the operator. The authorization level meter serves to measure the authorization level of the respective operator with the respective identity. It is also possible that the remote control apparatus comprises only the identifier (e.g. in the form of a biometric module or an RFID tag) and relays the identification data detected thereby to an external authorization level meter which can be provided on a central server.

In a first variant of the remote control apparatus, the coupling unit is designed as a transmitting unit (e.g., a transmitter). The transmitting unit serves to transmit a directed, optical prompt signal to the medical apparatus, in order to be able to establish bijective coupling between the remote control apparatus and the medical apparatus. In this embodiment, the coupling procedure is initiated by the remote control apparatus. This is effected by virtue of the fact that the remote control apparatus transmits the directed optical prompt signal to the medical apparatus. Alternatively, the prompt signal also may not be an optical prompt signal but instead a different type of prompt signal. The prompt signal can be used to transmit the identification code from the medical apparatus to the remote control apparatus.

In a second variation of the remote control apparatus, the coupling unit can be designed as a detecting unit (e.g., a detector) and can be configured to receive the identification code, which identifies the respective medical apparatus, on the remote control apparatus. The detecting unit can be designed as an optical sensor (e.g. camera) for detecting the QR identification code. If the identification code is provided as a bar code, the detecting unit is provided as a bar code scanner.

It is also possible to combine the two above-described embodiments of the remote control apparatus, so that the coupling unit is designed as a combined transmitting and detecting unit (e.g., a transceiver unit or a transceiver). In this case, the transmitting unit of the remote control apparatus transmits a prompt signal (optical or otherwise) to the medical apparatus. Subsequently, the medical apparatus can transmit the identification code back to the detecting unit. Furthermore, it is possible that the medical apparatus and/or the remote control apparatus additionally transmit(s) a confirmation code back to the respective other communication partner, in order to confirm the received signal and to initiate the coupling process.

In accordance with a further aspect, the invention relates to a medical apparatus which is designed having a signal exchanger (e.g., a transceiver unit or an identification code) which is configured to facilitate establishment of a bijective coupling between the remote control apparatus and the medical apparatus via a directed coupling signal; and a processing unit (e.g., a processor) which exchanges data with the signal exchanger and is configured to establish a coupling between the remote control apparatus and the medical apparatus.

In accordance with a further aspect, the invention relates to a remote control system for medical apparatuses, comprising:

a group of medical apparatuses, wherein all or selected ones of the medical apparatuses comprise a signal exchanger and a processing unit, and at least one remote control apparatus for remote control of at least one of the medical apparatuses, wherein the remote control apparatus comprises a coupling unit and a processing unit.

In accordance with a first exemplary embodiment of the remote control system, the coupling unit of the remote control apparatus is designed as a (preferably optical) detecting unit which is configured to receive an (optical or graphical) identification code which identifies the respective medical apparatus and wherein the signal exchanger of the medical apparatus is designed or provided as an optical identification code on the medical apparatus and wherein the processing unit of the remote control apparatus is configured to decode the received identification code, in order to establish bijective coupling between the remote control apparatus and the medical apparatus.

In accordance with a second exemplary embodiment, the coupling unit of the remote control apparatus is designed as a (preferably optical) transmitting unit which is configured to transmit a directed prompt signal to the medical apparatus and wherein the signal exchanger of the medical apparatus is designed as a transceiver unit (e.g., a transceiver) configured to receive the prompt signal of the transmitting unit and subsequently to transmit an optical identification code to the remote control apparatus, wherein the processing unit of the remote control apparatus is configured to receive and to decode the received identification code, in order to establish bijective coupling between the remote control apparatus and the medical apparatus and to establish a control channel.

As already described above, in the preferred embodiment the prompt signal is an optical signal, but it can also be formed by a different type of signal.

As already explained above, the medical apparatus can have a signalling device which is preferably optical in nature and via which feedback about the instantaneous coupling state can be provided. For instance, it is possible to signal whether coupling could be performed successfully (thus making the remote control functionality available) or whether the coupling has failed. It is also possible to signal whether parallel remote control is provided by a plurality of remote control apparatuses or whether a block has been put on the parallel multiple remote control functionality or not.

Furthermore, the remote control system can comprise a server which is configured to store different data sets. In particular, the different command sets can be stored herein. Furthermore, it is also possible to store a data-processing link between the identification code, the respective identity of the medical apparatus and a remote control code. These allocations can be interrogated via corresponding authorization measures by the remote control apparatus and/or by the medical apparatus. To this end, the apparatuses of the remote control system exchange data via a remote data transmission (e.g. according to the WLAN protocol or other communications protocols).

Such a remote data transmission to a central server likewise renders it possible to interrogate the identification code also for medical apparatus newly connected to the remote control system, so that the remote control can also be adapted for previously unknown medical apparatuses. Such downloading of new identification codes does not have to be associated with the reading-in of the graphical identification code. It is also possible that after optical initiation of a coupling process the medical apparatus transmits a different characterizing identification feature (e.g., a serial number, etc.) via radio communication (e.g., via WLAN) to the remote control apparatus which for its part links, or for the first time transfers from a server, the respectively allocated or matching identification code in the manner previously described. A distinction can be made between the identification codes of similar medical apparatuses via an individual key which can be combined with the actual identification code. For example, additionally transmitted identification bits can be used for this purpose. However, the adaptation of the identification code relates only to the situation where proprietary protocols are used for remote control purposes, in which each user intervention which is to be performed on the medical apparatus via the remote control apparatus is allocated a characteristic action code.

If the actual remote control is to be performed via a standard protocol (http, https, near field communication (NFC), Bluetooth, etc.), then it may be ensured that after the coupling process only one authorized connection of precisely the one medical apparatus to a dedicated remote control apparatus takes place.

In the following detailed description of the figures, exemplary embodiments, which are not to be understood to be limiting, together with features and further advantages will be discussed with the aid of the drawing.

FIG. 1 shows an overview of the system in an exemplary embodiment for remote control of medical apparatuses. As illustrated by way of example in FIG. 1, a remote control apparatus FG is to remote control a medical apparatus $MG_2$ in a dedicated manner. The medical apparatus $MG_2$ to be remote controlled belongs to a group of medical apparatuses $MG_1$, $MG_2$, $MG_3$ which can be arranged, for example, in a dialysis station. The medical apparatuses can be of a different design and can be designed as a hemodialysis apparatus, peritoneal dialysis apparatus or as other medical apparatuses. Typically, a medical apparatus comprises a graphical user interface which can be designed as a touch-screen and serves as an input and output interface or user interface. Furthermore, the medical apparatus has further interfaces, in particular to a central server. The medical apparatus comprises as a central unit an extracorporeal treatment module which is illustrated only schematically in FIG. 1 in the central region of the medical apparatus. The extracorporeal treatment module is used for purifying blood and comprises a multiplicity of operating components, such as a blood pump, substituate pumps, valves, syringes, brackets, receptacles and the like. The right-hand side of FIG. 1 illustrates such a pump which is connected to the medical apparatus via corresponding connection hoses. Furthermore, the apparatus comprises a support structure which comprises further mechanical, electrical, electronic and/or medical components.

The remote control apparatus FG is designed as a mobile apparatus, in particular as a smartphone, tablet or laptop. The remote control apparatus FG comprises a—preferably graphical—user interface.

In an exemplary embodiment, a common universal remote control FG is provided which renders it possible to activate in a dedicated manner a medical apparatus which is operated in a group of medical apparatuses or dialysis apparatuses. The remote control apparatus FG controls in each case precisely one medical apparatus in one time phase. This is intended to be indicated schematically by the two opposing arrows which connect the remote control apparatus FG and the medical apparatus $MG_2$. A connection between the remote control apparatus FG and the other medical apparatuses $MG_1$, $MG_3$ in the group of medical apparatuses is not to be operated by the remote control apparatus FG, if it is coupled to the medical apparatus $MG_2$. This situation is represented schematically in FIG. 1 by virtue of the fact that the opposing arrows for the bidirectional data exchange from the remote control apparatus FG in the direction of the first medical apparatus $MG_1$, and in the direction of the third medical apparatus $MG_3$ are indicated as being crossed out. In this case, the remote control system is operated with so-called single remote control functionality or in a so-called single remote control mode. This means that in one time phase the remote control apparatus FG can be coupled only to one medical apparatus of the group of medical apparatuses, in order to remote control said medical apparatus. Therefore, in the single remote control operating mode, a 1:1 allocation is provided between the medical apparatus $MG_2$ and the remote control apparatus FG. This setting can prevent other medical apparatuses from also being remote controlled when a remote control apparatus FG is coupled and when a command set for remote control of the medical apparatus is input accordingly. Of course, in the single remote control operating mode the same remote control apparatus FG can also be coupled to other medical apparatuses in a preceding or in a subsequent time phase, in order to remote control said medical apparatuses.

A correct coupling between the remote control apparatus FG and the medical apparatus provides for being able to preclude any manipulation during the remote control process. In order to safely remote control the medical apparatus, a specific communications interface between the universal remote control FG and the medical apparatuses is provided. A universal remote control FG, such as a smartphone or a mobile telecommunications apparatus, has a coupling unit which can be designed as a transmitting unit and/or as a detecting unit. In a preferred embodiment, the transmitting unit can be designed, for example, as an infrared diode or as a panel of infrared diodes, in order to transmit optical signals at a predetermined angle to the medical apparatus, in particular to a signal exchanger of the medical apparatus. To this end, a directed optical coupling signal can be exchanged between the remote control apparatus FG and the respective medical apparatus. In a preferred embodiment of the present invention the coupling signal is collimated or bundled. The collimated coupling signal may be generated via a collimating component at the sending unit, such as optical lenses or collimators. Preferably, a parallel bundle of light or a convergent bundle of light should be generated. This light bundling/collimation embodiment has the technical advantage that it is ensured that the user of the remote control apparatus FG is in visual contact and may directly view onto the medical apparatus to be remote controlled, and thereby also keeping an eye on the patient who is to be treated at the medical apparatus. This is to provide an additional safety aspect. In so doing, laser technology can be used which permits orientation with a specific target at a specific angle. Subsequently, the signal exchanger of the medical apparatus receives the optical coupling signal from the remote control apparatus and then instigates a coupling of the two apparatuses. In a simple embodiment, the signal exchanger can be designed as an infrared detecting module, in order to receive the infrared signals of the remote control apparatus FG. Therefore, the medical apparatus addressed by the remote control apparatus can detect if the remote control apparatus FG is aimed at the IR receiving module at the predetermined angle. Optionally, a confirmation signal can then be transmitted to the remote control apparatus FG which likewise is optionally acknowledged by the remote control apparatus FG. Furthermore, an acknowledgement signal can be output, in order to signify that the respectively previously transmitted signal has been correctly received and a coupling can be established between the respective medical apparatus and the remote control apparatus FG. Subsequently, i.e., after successful coupling, a control channel can be established between the remote control apparatus FG and the dedicated medical apparatus.

A coupling channel serves to exchange coupling signals which can be configured, for example, as a prompt signal, as an identification code, as a confirmation signal and/or as an acknowledgement signal and as a request command. The coupling channel and the control channel can be based upon different transmission technologies. Preferably, the control channel is based upon a radio link, such as a WLAN link, whereas the coupling channel is based upon an optical transmission, such as an infrared transmission. Alternatively, other radio-based and wireless communications techniques, such as Bluetooth, NFC or a proprietary Local Area Network (LAN) or Internet-based protocols can be used.

As shown schematically in FIG. 1, a first identification code $ID_1$ is provided on a first medical apparatus $MG_1$ and characterizes and identifies the apparatus, a second identification code $ID_2$ is provided on the second medical apparatus $MG_2$ and a third identification code $ID_3$ which identifies the third apparatus $MG_3$ is provided on the third apparatus $MG_3$. The identification code can be provided as a QR code, as a bar code or as a graphical code in a different format. The identification code can also be provided as an optical or acoustic signal.

Figure 2:
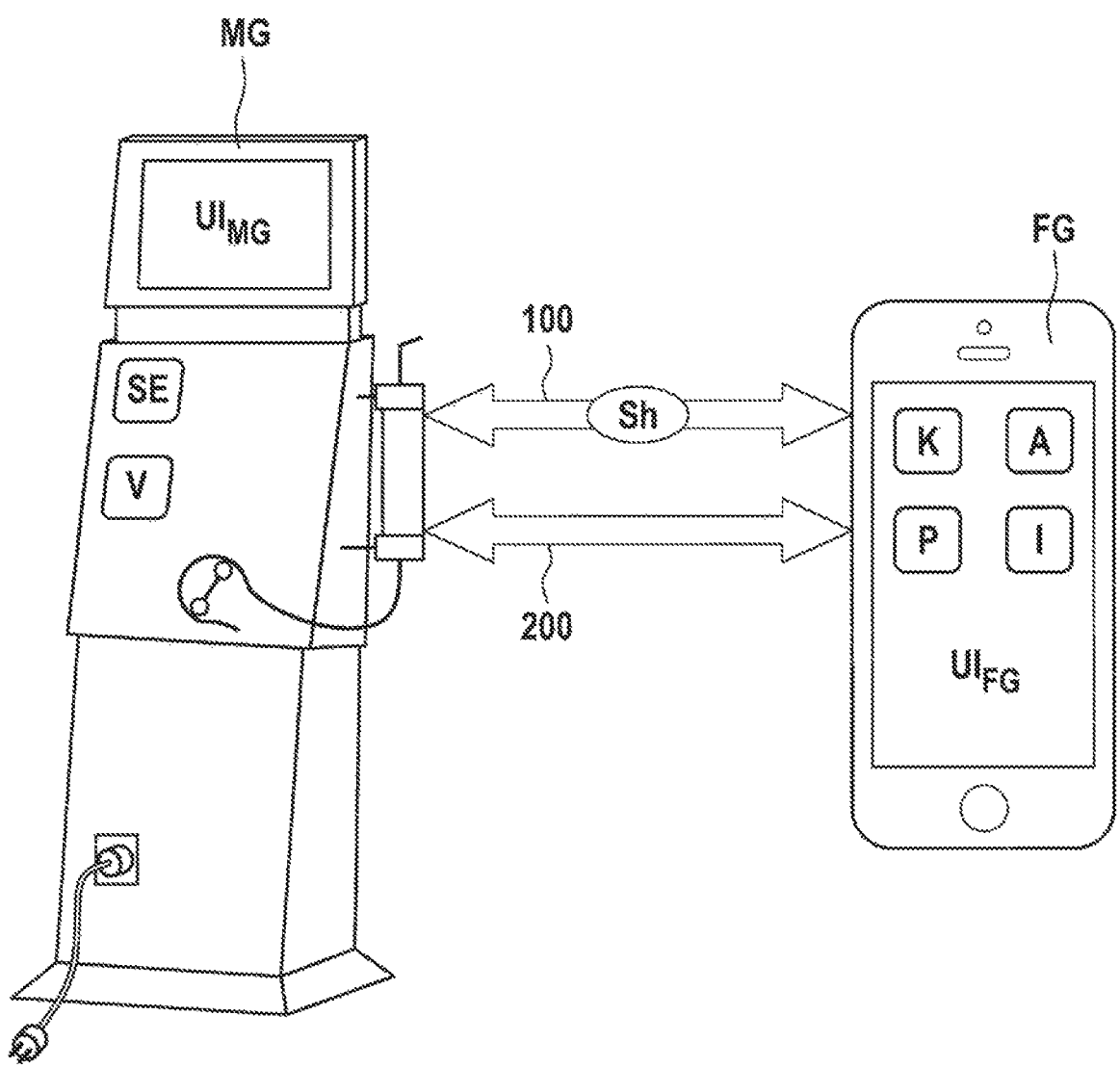
FIG. 2 shows a medical apparatus and a remote control apparatus and the relevant data exchange for establishing a coupling.

FIG. 2 shows in a likewise schematic illustration the data exchange between a remote control apparatus FG and a medical apparatus MG in a more detailed view. The medical apparatus MG is designed having a graphical user interface $UI_{MG}$ and comprises in addition a signal exchanger SE and a processing unit V. The signal exchanger SE is configured to facilitate exchanging a directed—preferably optical—coupling signal Sh between the remote control apparatus FG and the medical apparatus MG, in order to establish bijective coupling between the two communicating apparatuses. The signal exchanger SE may exchange data with the processing unit V. This serves to establish the coupling between the two apparatuses MG, FG. The remote control apparatus FG illustrated on the right-hand side of FIG. 2 comprises, in addition to the typical telecommunications components, a graphical user interface $UI_{FG}$ and a coupling unit K illustrated merely schematically in FIG. 2, and a likewise merely schematically illustrated processing unit P, which both exchange data. The coupling unit K serves to exchange the directed (preferably optical) coupling signal Sh between the apparatuses involved, in order to establish the coupling. The processing unit P serves to perform the remote control procedure by transferring commands or command sets and corresponding signals. The remote control procedure can only be initiated and performed after a coupling could be successfully established. It is important that the respective remote control apparatus FG controls a specific medical apparatus MG in a dedicated manner. The remote control apparatus FG can comprise an identifier I. The identifier I serves to automatically determine the identity of the operator (finger print scanner or biometric data detecting unit, etc.). These identification data can be relayed to an authorization level meter A which is configured to determine the authorization level and thus the functionality of the respective operator. The identifier I can be integrated into the authorization level meter A. It is also possible to form only the identifier I on the remote control apparatus FG and to form the authorization level meter A on another computer-based entity (e.g. a central server) which exchanges data with the remote control apparatus FG.

As already explained and schematically illustrated in FIG. 2, two different communications connections are provided between the remote control apparatus FG and the medical apparatus MG:

1. the coupling channel 100 for exchanging the coupling signal Sh and
2. the control channel 200 for transmitting control signals as part of the remote control procedure.

As further described herein, the signal exchanger SE may be implemented in different ways according to various exemplary embodiments, including, for example, as one or more scannable elements that may be scanned, e.g., optically, to provide the identification code to the remote control apparatus, and/or as a transceiver unit (e.g., a transceiver) that may communicate with the remote control apparatus.

Figure 3:
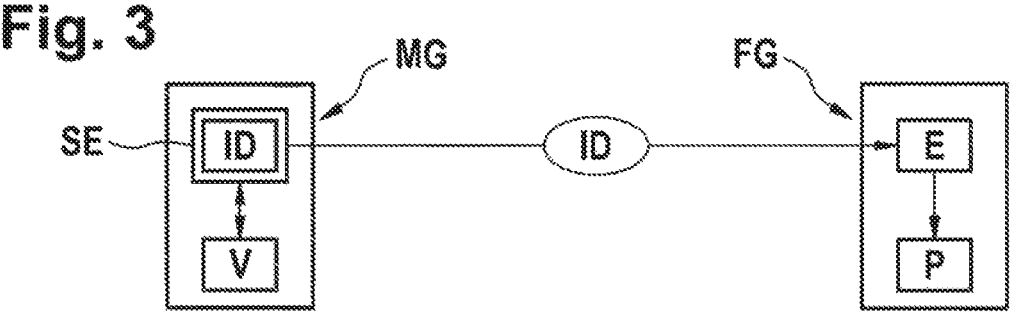
FIG. 3 shows a first exemplary embodiment of a coupling procedure for remote control of a medical apparatus using a remote control apparatus.

FIG. 3 shows a first exemplary embodiment of the method. In this embodiment, provision is made that all or selected ones of the medical apparatuses which are to be prepared for remote control are equipped with an identification code. In this case, the signal exchanger SE is designed, for example, as a QR code which can be provided directly on an easily accessible front side of a medical apparatus MG. The remote control apparatus FG illustrated on the right-hand side of FIG. 3 is designed having a detecting unit E which is configured to detect the identification code ID of the medical apparatus MG. If the identification code ID is provided as a graphical code (e.g. as a QR code), the detecting unit E is designed as a camera. If the signal exchanger SE is designed as a bar code, and therefore the identification code is provided via a bar code, the detecting unit E is provided on the remote control apparatus FG accordingly as a bar code scanner. In other words, the detecting unit E on the remote control apparatus FG serves to detect the identification code ID in its specific format. The detecting unit E exchanges data with a processing unit P which, after successful coupling, initiates the remote control procedure. To this end, the processing unit P can exchange data with the processing unit V of the medical apparatus MG.

Furthermore, it is possible that the remote control is configured to be geared even more specifically to the respective medical apparatus MG. To this end, further characteristics and parameters of the medical apparatus MG may be provided, which is to be remote controlled in each case, on the remote control apparatus. To this end, the remote control apparatus FG can transmit a prompt signal with a request command to the medical apparatus MG, in order to request further parameters which specify technical characteristics of the medical apparatus MG (e.g. design, type, serial number, interfaces etc.).

In one variation with respect to the exemplary embodiment explained in FIG. 3, provision can be made that, after successful reception of the identification code ID, the remote control apparatus FG transmits a confirmation signal to the medical apparatus MG, in order to signal to the medical apparatus that the identification code has been successfully received. Only then can the coupling be established between the communications entities involved.

Figure 4:
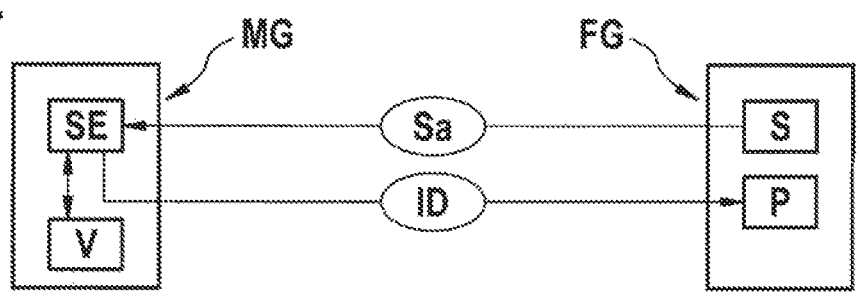
FIG. 4 shows a second exemplary embodiment for remote control of a medical apparatus using a remote control apparatus.

FIG. 4 shows a second exemplary embodiment of the method. Here, in contrast to the exemplary embodiment explained in greater detail above in conjunction with FIG. 3, a coupling signal is exchanged not in the form of the identification code ID but instead in the form of a prompt signal Sa. In this exemplary embodiment, the coupling procedure is thus initiated and triggered by the remote control apparatus FG. To this end, the coupling unit designed as a transmitting unit S transmits the prompt signal Sa to the medical apparatus MG. The signal exchanger SE, provided as a transceiver unit in this example, of the medical apparatus MG receives the prompt signal Sa and subsequently transmits the identification code ID, which identifies the respective apparatus, to the processing unit P of the remote control apparatus FG. In the simplest case, a successful coupling is thereby already established between the communication partners MG, FG involved. The medical apparatus MG can then be remote controlled by a command input on the user interface of the remote control apparatus FG.

However, in more complex embodiments it is still possible that in addition further data are exchanged between involved communication partners MG, FG. For instance, it is possible in particular that, after receiving the identification code ID, the remote control apparatus FG transmits a confirmation signal to the medical apparatus, in order to signal thereto that it has successfully received the identification code ID. Only then can the coupling be established between the medical apparatus MG and the remote control apparatus FG.

Figure 5:
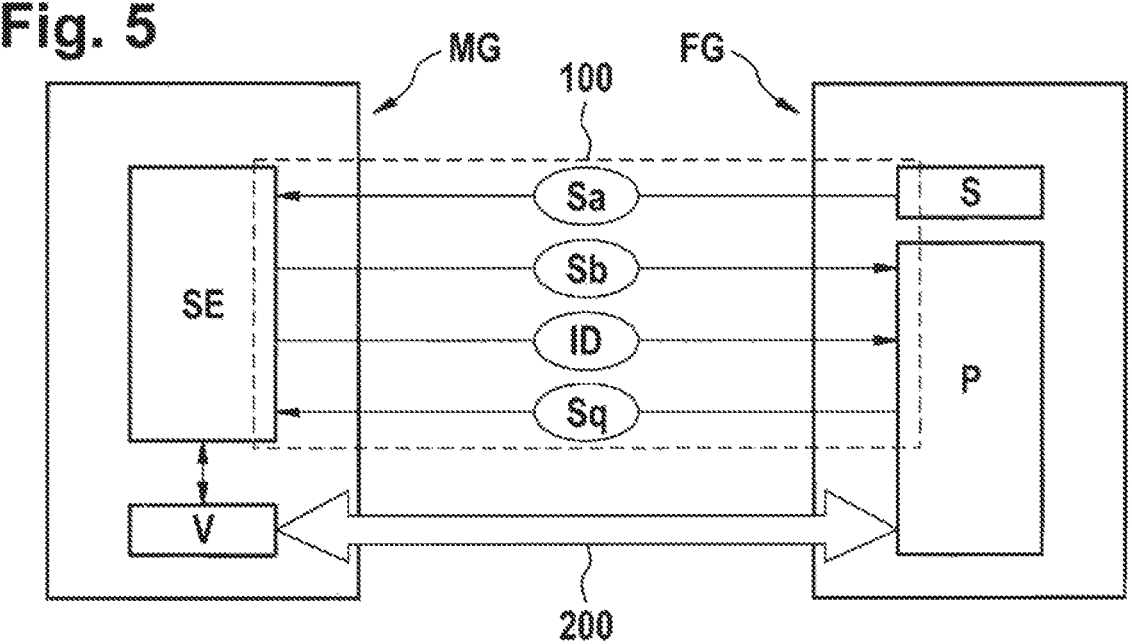
FIG. 5 shows in detail the data exchange between the remote control apparatus and the medical apparatus for establishing a coupling.

The above-described exemplary embodiments can also be combined in one embodiment. For instance, FIG. 5 shows a remote control system comprising the remote control apparatus FG and the medical apparatus MG. The coupling procedure is initiated by the remote control apparatus FG, in that the transmitting unit S transmits a prompt signal Sa to the signal exchanger SE (e.g., transceiver unit) of the medical apparatus MG. The signal exchanger SE receives this prompt signal Sa and can subsequently transmit the identification code ID either directly to the processing unit P of the remote control apparatus FG. However, the medical apparatus MG can alternatively also be configured to initially transmit a confirmation signal Sb to the processing unit P. After receiving the respective signal at the processing unit P, said device is configured to transmit an acknowledgement signal Sq to the signal exchanger SE of the medical apparatus MG. However, the transmission of the acknowledgement signal Sq is also only optional and is not absolutely necessary. Therefore, the safety of the coupling procedure can be increased. After successful coupling which is performed via the coupling channel 100, the remote control function can be initiated via the control channel 200. The control channel 200 can be formed preferably between the processing unit V of the medical apparatus MG and the processing unit P of the remote control apparatus FG.

In FIG. 5, the coupling channel 100 is represented in the rectangle illustrated by the broken lines. The signals required for the coupling procedure are exchanged via the coupling channel 100. In addition, a different control channel 200 which deviates from the coupling channel 100 can be formed, in order to be able to perform efficient remote control by rapid transmission of the control commands.

Figure 6:
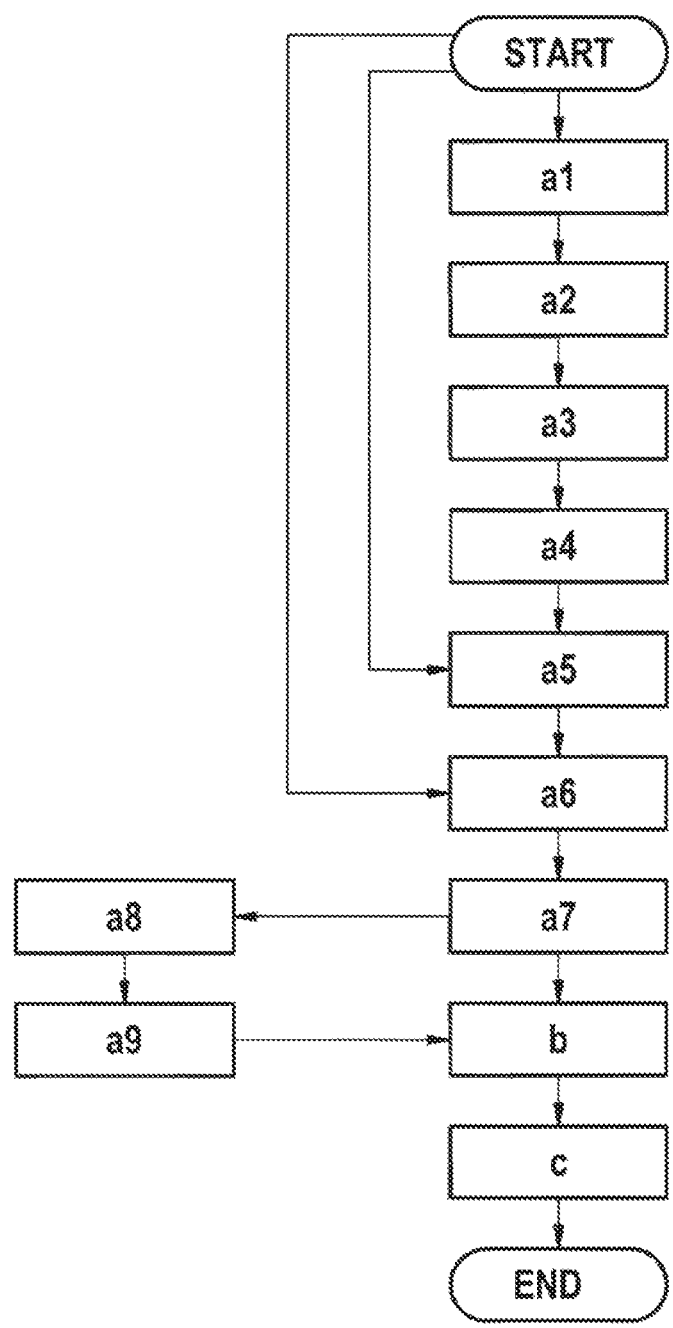
FIG. 6 shows a flow diagram for establishing a coupling in accordance with an exemplary embodiment.

A possible sequence of the method in an exemplary embodiment is explained in greater detail hereinafter with reference to FIG. 6 including several variations.

After the start of the method, in step a1 a prompt signal Sa can be transmitted by the remote control apparatus FG to the medical apparatus MG. In step a2, the prompt signal Sa is received on the medical apparatus MG. In step a3, a confirmation signal Sb is transmitted to the remote control apparatus FG. In step a4, the confirmation signal Sb is received on the remote control apparatus FG. In step a5, the identification code ID is transmitted by the medical apparatus MG to the remote control apparatus FG. In one development, the identification code ID comprises additional technical parameters which specify the respective medical apparatus MG in greater detail, in order to be able to adapt the remote control procedure specifically to the medical apparatus MG. Furthermore, the medical apparatus MG can have a parameter set stored thereon which denotes the form and scope in which remote control of the medical apparatus is to be possible. In this case, these parameters are also transmitted to the remote control apparatus FG, in order to be taken into account for the subsequent remote control procedure 200. The above-described embodiment corresponds approximately to the embodiment explained above with reference to FIG. 5.

However, it is alternatively and preferably possible to not transmit the confirmation signal Sb after reception of the prompt signal Sa but instead to provide a different sequence of the method steps. In particular, it is possible to initially perform method step a1 with the transmission of the prompt signal. Subsequently, method step a5 can be performed, in order to transmit the identification code from the medical apparatus MG to the remote control apparatus FG. Subsequently, the confirmation signal Sb can be transmitted. In this case, the confirmation signal Sb serves to signal the reception of the identification code ID on the remote control apparatus FG. After reception of the identification code in step a6 on the remote control apparatus FG, the identification code ID can be decoded in step a7. In accordance with one exemplary embodiment, step b can then be performed, in that a coupling is established between the remote control apparatus FG and the medical apparatus MG. In step c, the control channel 200 can then be established between the communication entities FG, MG involved.

Alternatively, after step a7 the method can branch off to step a8. In step a8, characteristics of the remote control apparatus FG and/or of the respective user of the remote control apparatus FG are detected. This can be in particular an authorization scope of the user. The authorization scope indicates the remote control commands for which the respective user is authorized. In subsequent method step a9, the scope of the remote control functionality can then be detected. The scope of the remote control functionality can be calculated in dependence upon the detected technical characteristics of the medical apparatus MG and in dependence upon the detected authorization scope of the user of the remote control apparatus FG. Subsequently, a coupling can be established between remote control apparatus FG and the medical apparatus MG in step b. When the coupling is being established, the detected data are taken into account. In other words, a coupling channel is established which is designed exclusively for transferring control commands which correspond to the detected authorization scope of the user of the remote control apparatus and the detected remote control functionality. After the control channel has been established in step c, the method can end or can be performed repeatedly. The control method can also be applied to a different medical apparatus MG.

Basically, in a further exemplary embodiment the coupling can also be made to be dependent upon other parameters. For instance, provision can be made that the processing unit P of the remote control apparatus FG recognizes the distance at which the remote control apparatus FG is located from the medical apparatus MG to be remote controlled. A successful coupling can be established only if the distance is in a predeterminable desired range (e.g. between 1 to 5 metres).

Furthermore, it is possible to detect the angle at which the remote control apparatus FG transmits the prompt signal Sa to the medical apparatus MG. The prompt signal Sa can be successfully detected and acknowledged on the medical apparatus only in a specific angle range. It is also possible that a successful coupling is established only if the identification code ID could be detected in sufficient quality on the remote control apparatus FG.

Basically, the coupling state is indicated in the form of a coupling state signal. In the simplest case, an optical signal unit on at least one of the two communication entities MG, FG is used for this purpose. In alternative embodiments, the signal unit can also be configured to represent the coupling state only on one of the communication partners involved. Furthermore, after outputting the coupling state a corresponding field can be formed on the user interface $UI_{MG}$, $UI_{FG}$ which the user can then actuate. For example, he can press an "OK" button, in order to signal that the intended coupling between the respective medical apparatus MG and the respective remote control apparatus FG is permitted. Only when the manually input confirmation signal is received can a coupling be successfully performed. Furthermore, this feature increases safety because it includes a visual contact between the medical apparatus MG to be remote controlled and the remote control apparatus FG.

As already described above, the scope of the remote control can be limited or extended in dependence upon different parameters and variables. In the simplest case, the entire functionality of the medical apparatus can be remote controlled. Therefore, the entire interface of the medical apparatus MG is mapped to the interface of the remote control apparatus $UI_{FG}$. However, it is also possible to restrict the remote control functionality to specific command sets depending upon the technical parameters of the medical apparatus MG and/or upon the authorization level of the user.

Preferably, specific user groups can be defined, to which a specific authorization level is allocated in each case. For example, all senior doctors can have a specific authorization level, whereas nurses can have a different authorization level.

The authorization level or the authorization scope and further rules for controlling the remote control process can be stored at a central location, for example, on a server. These settings can be changed at any time, without it being necessary to have to make settings on the medical apparatus MG or on the remote control apparatus FG. Therefore, it is possible to set which remote control functionalities are to be available.

An advantage of the system in an exemplary embodiment can be seen in the fact that a medical apparatus MG can also be remote controlled in a contactless manner. This greatly reduces the risk of cross-contamination. It is no longer necessary for the operating person to stand directly in front of the medical apparatus, instead the medical apparatus MG can also be remote controlled outside the room by a remote control apparatus FG.

Finally, it is noted that the description of the invention and the exemplary embodiments are fundamentally to be understood to be non-limiting with respect to a specific physical implementation of the invention. All features explained in conjunction with individual embodiments of the invention and illustrated in the figures can be provided in different combinations in the subject matter in accordance with the invention, in order to achieve the advantageous effects thereof at the same time. The different features and embodiments can also be combined.

It will be appreciated that the invention can be used not just for dialysis apparatuses but also for other medical apparatuses. Furthermore, the remote control apparatuses can be formed not only by smartphones but also by other electronic components having a corresponding user interface.

It is also within the scope of exemplary embodiments of the invention to provide a different sequence of the method steps. In particular, confirmation signals can be transmitted—optionally—after each or predeterminable exchanged signal(s). For example, it is also possible that after the identification code ID is transmitted by the medical apparatus MG to the remote control apparatus FG a confirmation signal Sb is transmitted. The confirmation signal Sb confirms in this case the complete and correct reception of the identification code ID. However, this is only optional. In the simplest case, merely one identification code ID can be exchanged, in order to establish a successful coupling. The data which is held available and stored can be stored either locally or at a central location. The latter has the advantage that said data can also be changed without changing the communication partners and can also be accessible for other entities. It is also within the scope of exemplary embodiments of the invention in this case to define further measures and regulations for a successful coupling. For example, it is possible to define that a coupling can be performed only at specific time phases. It can also be preset that a coupling can be performed only by a specific circle of users.

The scope of protection of the present invention is set by the claims and is not limited by the features explained in the description and shown in the figures.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for contactlessly establishing remote control of a dialysis apparatus of a group of dialysis apparatuses using a mobile remote control apparatus, comprising:
   in a coupling phase:
      exchanging a directed optical coupling signal between the mobile remote control apparatus and the dialysis apparatus to ensure a user of the mobile remote control apparatus is in visual contact with the dialysis apparatus, wherein the directed optical coupling signal corresponds to light-based communication; and
      after exchanging the directed optical coupling signal between the mobile remote control apparatus and the dialysis apparatus, transmitting, by the dialysis apparatus, a confirmation signal to the mobile remote control apparatus, and outputting, by the mobile remote control apparatus, an acknowledgement signal in response to the confirmation signal; and
   establishing, in response to successful completion of the coupling phase, after transmission of the confirmation signal and/or output of the acknowledgement signal, a radio-based control channel between the mobile remote control apparatus and the dialysis apparatus, wherein the radio-based control channel is used for bidirectional exchange of control signals between the mobile remote control apparatus and the dialysis apparatus via radio-based communication.

2. The method according to claim 1, wherein exchanging the directed optical coupling signal between the mobile remote control apparatus and the dialysis apparatus comprises:
   transmitting a directed optical prompt signal by the mobile remote control apparatus to the dialysis apparatus; or
   receiving an identification code, which identifies the dialysis apparatus, on the mobile remote control apparatus.

3. The method according to claim 2, wherein the optical prompt signal comprises a request command for requesting parameters which represent characteristics of the dialysis apparatus.

4. The method according to claim 1, wherein outputting the acknowledgement signal comprises outputting the acknowledgement signal on the mobile remote control apparatus or transmitting the acknowledgement signal to the dialysis apparatus.

5. The method according to claim 1, wherein an identification code or the confirmation signal is received and decoded on the mobile remote control apparatus in order to identify the dialysis apparatus to be remote controlled and to determine a command set for remote control purposes.

6. The method according to claim 1, wherein a coupling state is detected and output on the dialysis apparatus and/or on the mobile remote control apparatus.

7. The method according to claim 6, wherein the coupling state is represented by a coupling state signal, a remote control signal and/or a multiple remote control signal.

8. The method according to claim 1, wherein for remote control of the dialysis apparatus, a user interface of the dialysis apparatus is transferred to the mobile remote control apparatus.

9. The method according to claim 1, wherein the remote control of the dialysis apparatus is configured to be limited or extended in response to a detected authorization signal, which represents an authorization scope of the user of the mobile remote control apparatus, and/or in response to the confirmation signal or an identification code of the dialysis apparatus.

10. The method according to claim 1, wherein different command sets for performing remote control of the dialysis apparatus are stored and a specific command set is determined based on a detected authorization level of the user.

11. The method according to claim 1, wherein an input command of a command set for remote control of the dialysis apparatus by a first user is configured to be overwritten by a second user in response to a detected correction command of the second user if the authorization level of the second user is higher than that of the first user.

12. The method according to claim 1, wherein a multiple remote control functionality for remote control of the dialysis apparatus is configured to be activated or deactivated sequentially and/or in parallel by a plurality of remote control apparatuses.

13. The method according to claim 1, wherein further coupling to a second remote control apparatus is configured to be effected in response to a multiple remote control criterion having been successfully verified.

14. The method according to claim 1, wherein only the radio-based communication and not the light-based communication is used for transferring remote control commands from the mobile remote control apparatus to the dialysis apparatus.

15. The method according to claim 1, wherein the mobile remote control apparatus is coupled to multiple dialysis apparatuses via respective light-based communications, and the mobile remote control apparatus controls each of the multiple dialysis apparatuses via respective radio-based communications.

16. The method according to claim 1, wherein the mobile remote control apparatus is configured to be connected to only one dialysis apparatus to avoid unauthorized access.

17. A remote control apparatus for remote control of a dialysis apparatus, the remote control apparatus comprising:
   a first interface configured for optical communication;
   a second interface configured for radio-based communication; and
   a processor configured to:
      in a coupling phase: exchange, via the first interface, a directed optical coupling signal between the remote control apparatus and the dialysis apparatus to ensure a user of the remote control apparatus is in visual contact with the dialysis apparatus, wherein the directed optical coupling signal corresponds to light-based communication, and after exchanging the directed optical coupling signal between the remote control apparatus and the dialysis apparatus, receive a confirmation signal from the dialysis apparatus and output an acknowledgement signal in response to the confirmation signal; and
      in response to successful completion of the coupling phase, after reception of the confirmation signal and/or output of the acknowledgement signal, establish a radio-based control channel between the remote control apparatus and the dialysis apparatus, wherein the radio-based control channel facilitates bidirectional exchange of control signals between the remote control apparatus and the dialysis apparatus via the second interface.

18. The remote control apparatus according to claim 17, wherein the remote control apparatus further comprises:
   a user interface, configured to receive user input for remote control of the dialysis apparatus.

19. The remote control apparatus according to claim 17, wherein the remote control apparatus further comprises:
   an authorization level meter and/or an identifier.

20. The remote control apparatus according to claim 17, wherein the first interface comprises a transmitter, configured to transmit a directed optical prompt signal to the dialysis apparatus.

21. The remote control apparatus according to claim 17, wherein the first interface comprises a detector, configured to receive an identification code which identifies the dialysis apparatus.

22. A dialysis apparatus, comprising:
   a first interface configured for optical communication;
   a second interface configured for radio-based communication; and
   a processor configured to:
      in a coupling phase: exchange, via the first interface, a directed optical coupling signal between the remote control apparatus and the dialysis apparatus to ensure a user of the remote control apparatus is in visual contact with the dialysis apparatus, wherein the directed optical coupling signal corresponds to light-based communication, and after exchanging the directed optical coupling signal between the remote control apparatus and the dialysis apparatus, transmit a confirmation signal to the remote control apparatus; and
      in response to successful completion of the coupling phase, after transmission of the confirmation signal and/or output of an acknowledgement signal, establish a radio-based control channel between the remote control apparatus and the dialysis apparatus, wherein the radio-based control channel facilitates bidirectional exchange of control signals between the remote control apparatus and the dialysis apparatus via the second interface.

23. A remote control system for dialysis apparatuses, the remote control system comprising:
   a dialysis apparatus; and
   a remote control apparatus;
   wherein the remote control apparatus and the dialysis apparatus are configured to, in a coupling phase, exchange a directed optical coupling signal for ensuring a user of the remote control apparatus is in visual contact with the dialysis apparatus, wherein the directed optical coupling signal corresponds to light-based communication;
   wherein the dialysis apparatus is configured to, in the coupling phase, after exchanging the directed optical coupling signal between the remote control apparatus and the dialysis apparatus, transmit a confirmation signal to the remote control apparatus;
   wherein the remote control apparatus is configured to, in the coupling phase, in response to the confirmation signal, output an acknowledgement signal; and
   wherein the remote control apparatus and the dialysis apparatus are further configured to, in response to successful completion of the coupling phase, after transmission of the confirmation signal and/or output of the acknowledgement signal, establish a radio-based control channel between the remote control apparatus and the dialysis apparatus, wherein the radio-based control channel facilitates bidirectional exchange of control signals between the remote control apparatus and the dialysis apparatus via radio-based communication.

24. The remote control system according to claim 23, wherein the remote control apparatus is further configured to receive an identification code which identifies the dialysis apparatus;
   wherein the dialysis apparatus comprises an optical identification code on the dialysis apparatus; and
   wherein the remote control apparatus is further configured to decode the identification code of the dialysis apparatus.

25. The remote control system according to claim 23, wherein the remote control apparatus is further configured to transmit a directed optical prompt signal to the dialysis apparatus;
   wherein the dialysis apparatus is further configured to receive the prompt signal and subsequently to transmit an optical identification code to the remote control apparatus;
   wherein the remote control apparatus is further configured to receive and decode the identification code.

* * * * *